US008613906B2

(12) United States Patent
Muhs et al.

(10) Patent No.: US 8,613,906 B2
(45) Date of Patent: Dec. 24, 2013

(54) TREATMENT OF ISCHEMIA USING STEM CELLS

(75) Inventors: Andreas Muhs, Pully (CH); Stephan Wnendt, Aachen (DE)

(73) Assignee: ViaCord, LLC, Waltham, MA (US)

( * ) Notice: Subject to any disclaimer, the term of this patent is extended or adjusted under 35 U.S.C. 154(b) by 1077 days.

(21) Appl. No.: 11/915,660

(22) PCT Filed: May 26, 2006

(86) PCT No.: PCT/US2006/020290
§ 371 (c)(1),
(2), (4) Date: Jan. 27, 2009

(87) PCT Pub. No.: WO2006/130433
PCT Pub. Date: Dec. 7, 2006

(65) Prior Publication Data
US 2009/0214481 A1    Aug. 27, 2009

Related U.S. Application Data

(60) Provisional application No. 60/685,614, filed on May 27, 2005.

(51) Int. Cl.
*A61K 49/00* (2006.01)
(52) U.S. Cl.
USPC .......................................................... 424/9.1
(58) Field of Classification Search
USPC .......................................................... 424/9.1
See application file for complete search history.

(56) References Cited

U.S. PATENT DOCUMENTS

2002/0164794 A1   11/2002   Wernet

FOREIGN PATENT DOCUMENTS

| JP | 2004-521617 | 7/2004 |
| JP | 2004-529858 | 9/2004 |
| WO | WO 02/34272 | 5/2002 |
| WO | WO 02/36751 | 5/2002 |
| WO | WO 2005/063303 | 7/2005 |

OTHER PUBLICATIONS

Aoki et al. "Derivation of functional endothelial progenitor cells from human umbilical cord blood mononuclear cells isolated by a novel cell filtration device", Stem Cells, 2004, 22:994-1002.*
De Silva et al. "Delivery and tracking of therapeutic cell preparations for clinical cardiovascular applications", Cytotherapy, 2004m 6(6):608-614.*
Dengler et al. "Stem cell therapy for the infarcted heart", Herz, 27:598-610.*
Köegler et al., "A New Human Somatic Stem Cell from Placental Cord Blood with Intrinsic Pluripotent Differentiation Potential," *Journal of Experimental Medicine* 200:123-135 (2004).
Quesenberry et al., "Stem Cell Biology and the Plasticity Polemic," *Experimental Hematology* 33:389-394 (2005).
International Search Report of PCT/US06/20290 mailed Jun. 26, 2008.
Kögler et al., "Cytokine Production and Hematopoiesis Supporting Activity of Cord Blood-Derived Unrestricted Somatic Stem Cells," *Exp. Hematol.* 33:573-583, 2005.
Yang, "Transplantation of Endothelial Progenitor Cells from Cord Blood CD133+ Cells Augments the Neovascularization in Murine Ischemic Limb," *Exp. Hematol.* 31:182, 2003 (Abstract).
Yang et al., "Enhancement of Neovascularization with Cord Blood CD133+ Cell-Derived Endothelial Progenitor Cell Transplantation," *Thromb. Haemost* 91:1202-1212, 2004.
Supplemental European Search Report for European Application No. 06771203.4 dated Dec. 16, 2010.
Ahn et al., "Cord Blood Derived Mesenchymal Stem Cell Injection Into Ischemia-Reperfusion Myocardial Injury Decreases Fibrosis, Apoptosis, and Significantly Preserves Ventricular Systolic Function," *Circ. J.* 69: 396-397, 2005.
Japanese Patent Office Action (JP 2008-513716) and its English translation dated Nov. 17, 2011.
Li et al., "Beneficial effect of human unrestricted somatic stem cell transplantation on infarcted heart function: Preclinical study in porcine model," 77th Scientific Meeting of the American Heart Association 110(17): 325 (Abstract only) (2004).
Extended European Search Report for European Patent Application No. 13001977.1, dated Oct. 14, 2013 (6 pages).

* cited by examiner

*Primary Examiner* — Bin Shen
(74) *Attorney, Agent, or Firm* — Clark & Elbing LLP; Todd Armstrong

(57) ABSTRACT

The invention features a method for treating or preventing ischemia in a mammal by administering unrestricted somatic stem cells (USSCs) to the mammal.

17 Claims, No Drawings

TREATMENT OF ISCHEMIA USING STEM CELLS

CROSS-REFERENCE TO RELATED APPLICATIONS

This application is the U.S. National Stage of International Application No. PCT/US2006/020290, filed on May 26, 2006, which claims the benefit of U.S. Provisional Patent Application No. 60/685,614, filed on May 27, 2005; each of which is hereby incorporated by reference in their entirety.

BACKGROUND OF THE INVENTION

A number of U.S. Patents, e.g., U.S. Pat. Nos. 5,486,359; 5,591,625; 5,736,396; 5,811,094; 5,827,740; 5,837,539; 5,908,782; 5,908,784; 5,942,225; 5,965,436; 6,010,696; 6,022,540; 6,087,113; 5,858,390; 5,804,446; 5,846,796; 5,654,186; 6,054,121; 5,827,735; 5,906,934 disclose mesenchymal stem cells (MSC), which can be differentiated into several progenitor cells, for example muscle progenitor cells, connective tissue cell progenitors or oval cells. Muscle progenitor cells differentiate further into cardiac, skeletal as well as smooth muscle cells whereas the connective tissue cell progenitor may differentiate into bone.

U.S. application Ser. No. 09/985,335 (hereby incorporated by reference), describes somatic stem cells known as unrestricted somatic stem cells (USSCs), which can be derived from human umbilical cord blood, placental blood and/or the blood from a newborn child. USSCs are distinct from but capable to differentiate into mesenchymal stem or progenitor cells, hematopoietic lineage stem or progenitor cells, neural stem or progenitor cells, or endothelial stem or liver progenitor cells. USSCs represent the progenitor of the hematopoietic lineage, the mesenchymal stem cells as well as neural stem cells. This unique multifunctional capacity and the technology to expand these cells, either as cells that remain stem cells, or as committed cells under distinct differentiation protocols, allows precise characterization, standardization and utilization of the cells for the production and implementation of stem cell therapy in regenerative medicine. (Some of the text herein describing the isolation and culture of USSCs is taken from the aforementioned PCT and U.S. applications.)

SUMMARY OF THE INVENTION

We have discovered that USSCs possess the ability to treat and prevent ischemia by reconstituting blood flow.

Accordingly, the invention features a method for treating or preventing ischemia in a mammal having tissue in which ischemia, or the risk of ischemia, is associated with compromised blood flow to the tissue; the method involves administering unrestricted somatic stem cells (USSCs) to the mammal. In an embodiment, approximately $1 \times 10^5$ to $1 \times 10^9$ USSCs are administered to the patient, preferably about $2 \times 10^6$ USSCs are administered to the patient.

The invention is of particular importance in restoring cardiac function following any event or procedure involving the heart in which ischemia has occurred or is likely to occur. The most important use will be found in patients who have recently experienced myocardial infarction. Other cardiac patients include those who can benefit from the administration of USSCs, including patients who have undergone heart surgery and are at risk of reperfusion damage; e.g., patients who have undergone cardiac bypass procedures, valve repairs or replacements, heart transplantation, or balloon angioplasty.

Other ischemic conditions that can be treated or prevented according to the invention include ischemic events involving other internal organs such as the lungs, liver, and kidneys; regions containing skeletal muscle, e.g., limbs and trunk muscles; and ischemic conditions involving smooth muscle, e.g. surgeries involving the smooth muscle of the gastrointestinal tract, e.g., surgeries to treat lesions of the organs of the gastrointestinal tract, and surgeries to correct blockages, e.g., intestinal blockages.

A preferred method of administering USSCs is to administer the cells intravenously. Following intravenous administration, USSCs home to the site of ischemic damage, and graft in the region of such damage, bringing about the formation of new blood vessels which carry oxygen to the site of ischemic damage, reducing ischemia, thereby reducing the amount of atrophic muscle in the region.

Alternatively, USSCs can be administered to treat ischemia by administering the cells locally, e.g., intramuscularly, at or near the site of ischemic damage. Such local administration of cells may be advantageous in instances where the site of damage has particularly compromised blood flow, e.g., where ischemia in an extremity of a diabetic patient is to be ameliorated.

In the case of a patient who has experienced myocardial infarction, between approximately $2 \times 10^6$ and $1 \times 10^9$ USSCs suspended in a pharmaceutically acceptable buffer are administered to the patient intravenously as soon as possible, and preferably within 24 hours, after onset of the myocardial infarction. Other appropriate treatment regimens are employed at the same time. The blood flow to the heart is evaluated after two weeks; this involves standard oxygenation tests, and can also involve angiography, which can determine that the USSCs have brought about increased collateral blood vessel supply to the heart. If desired, additional USSCs can be administered at this time to further increase collateral circulation.

USSCs can be isolated and purified by the steps of density gradient isolation, culture of adherent cells, and subculture applying growth factors as described below. After a confluent cell layer has been established, the isolation process to derive USSCs is controlled by morphology (fibroblastoid morphology) and phenotypical analyses using antibodies directed against CD13 (positive) CD45 (negative), and CD29 (positive) surface antigens.

USSCs are negative for markers specific for the hematopoietic lineage such as CD45 and hence are distinct from hematopoietic stem cells, which can also be isolated from placental cord blood. CD14 and CD106 are two additional surface antigens that cannot be detected on USSCs. USSCs can be identified by the expression of one or more of the following cell surface markers: CD13, CD29, CD44, and CD49e. USSC preparations are further characterized by the presence of mRNA transcripts for certain receptor molecules like epidermal growth factor receptor (EGF-R), platelet derived growth factor receptor alpha (PDGF-RA), and insulin growth factor receptor (IGF-R). These cells also typically express transcription factors such as YB1 (Y-box transcription factor 1), Runx1 (runt related transcription factor 1) and AML1C (acute myeloid leukemia 1 transcription factor) as detected by RT-PCR. USSC preparations are typically negative for transcripts for the chondrogenic transcription factor Cart-1 and neural markers such as neurofilament, synaptophysin, tyrosine hydroxylast (TH) and glial fibriallary acidic protein (GFAP).

TABLE 1

Analysis of the transcription patterns of USSCs by RT PCR

| Name | PCR-Result USSC | PCR-result (other tissue) |
|---|---|---|
| PDGFR_alpha | + | +(adult bone) |
| IGFR | + | +(adult bone) |
| Neurofilament | − | +(adult liver) |
| CD 105 | + | +(mononuclear cells from CB) |
| GFAP | − | +(fetal brain) |
| Synaptophysin | − | +(fetal brain) |
| Tyrosinhydroxylase | − | +(fetal brain) |
| YB1 | + | +(fetal brain) |
| Runx1 | + | +(adult bone) |
| AML1c | + | +(adult bone) |
| BMPR II | + | +(adult cartilage) |
| Collagen Type I | + | +(adult bone) |
| Cart-1 | − | +(mononuclear cells from CB) |
| Chondroadherin | − | +(adult bone) |
| CD49e | + | +(adult bone) |

RT-PCR results achieved with predicted oligonucleotide primers and mRNAs from USSCs and positive control mRNAs from other tissues like bone, cartilage, brain or cord blood mononuclear cells.

The RAN expression of USSC preparations and bone marrow derived MSCs (Caplan, 1991) were directly compared by using quantitative Affymetrix GeneChip™ microarrays. The transcript of the fibulin-2 gene (gene bank number X82494) was detected in USSCs at a high expression levels but not in MSCs. Fibulin-2 production was previously demonstrated in fibroblasts (Pan et al., 1993). Northern blot analysis of mRNA from various human tissues reveals an abundant 4.5 kb transcript in heart, placenta and ovary tissue (Zhang et al., 1994). The protein has been localized at the light microscopical level in human embryos of gestational weeks 4-10, using polyclonal antibodies. Fibulin-2 was detected primarily within the neurophithelium, spinal ganglia and peripheral nerves (Misoge et al., 1996).

In the rat animal model, rat liver myofibroblasts (rMF) are localized with fibulin 2. These cells were located in the portal field, the walls of central veins, and only occasionally in the parenchyma. In early stages of fibrosis rMF were detected within the developing scars. In advanced stages of fibrosis rMF accounted for the majority of the cells located within the scar (Knittel et al., 1999). In an other animal model, mouse Fibulin-2 protein is express during epithelial-mesenchymal transformation in the endocardial cushion matrix during embryonic heart development. Fibulin-2 is also synthesized by the smooth muscle precursor cells of developing aortic arch vessels and the coronary endothelial cells that originate from neural crest cells and epicardial cells, respectively (Tsuda et al., 2001).

The transcripts of the Hyaluronan Synthase gene (D84424), Fibromodulin gene (U0 5291) and the transcript 1NFLS (W03846) were not detected in USSCs, but are detected at high levels in MSCs. Northern blot analysis indicated that Hyaluronan Synthase is ubiquitously expressed in human tissues (Itano and Kimata, 1996). The product of this enzyme, Hyaluronan, serves a variety of functions, including space filling, lubrication of joints, and provision of a matrix through which cells can migrate (Hall et al., 1995). Fibromodulin is a member of a family of small interstitial proteoglycans. The protein exhibits a wide tissue distribution, with the highest abundance observed in articular cartilage, tendon, and ligament (Sztrolovics et al., 1994). The transcript 1NFLS was cloned from human fetal liver.

The CD24 gene (L33930) is expressed at a very low level in USSCs, compared with the expression level in the MSCs. CD24 is expressed in may B-lineage cells and on mature granulocytes (Van der Schoot et al., 1989).

USSCs are characterized by the lack of expression of human leukocyte antigen class I (HLA-class I). In contrast to USSCs, the previously described MSCs isolated from bone marrow and muscle tissue, express very high levels of HLA-class I antigen on their cell surface. USSCs also express the stage specific early antigen 4 (SSEA4).

Typically, USSCs show a fibroblastoid cell shape and proliferate in an adherent manner. USSCs are also approximately 30% larger than MSCs. Thus, USSCs can be distinguished from MSCs morphologically.

USSCs can be present in a plurality of mixtures representing precursors of other somatic stem cells, e.g. of the hematopoietic lineage expressing AC 133 and CD34, mesenchymal progenitor somatic stem cells, neuronal progenitor somatic stem cells, or combinations thereof. Such combinations provide high regenerative potential based on the capability to differentiate into other, different somatic stem cells.

Some medicaments useful in the invention contain USSCs together with other somatic stem cells. The medicament may further contain carrier substances or auxiliary substances, which are medically and pharmacologically acceptable. USSCs may be administered directly or together with pharmaceutically acceptable carriers or adjuvants. It may be advantageous to add additional therapeutically active substances which treat ischemia.

Generally, methods known for the administration of MSCs can be applied in an analogous manner when administering USSCs. For example, the administration of stem cells is described in B. E. Strauer et al. M. "Intrakoronare, humane autologe Stammzelltransplantation zur Myokardregeneration nach Herzinfarkt", Dtsch. Med. Wochenschr 2001; 126: 932-938; Quarto R., et al., "Repair of Large Bone Defects with the Use of Autologous Bone Marrow Stromal Cells". N. Eng. J. Med. 2001; 344:385-386; Vacanti C. A., "Brief Report: Replacement of an Avulsed Phalanx with Tissue-Engineered Bone" N. Eng. J. Med. 2001; 344:1511-1514, May 17, 2001; Hentz V. R., "Tissue Engineering for Reconstruction of the Thumb", N. Eng. J. Med. 2001; 344:1547-1548; Brittberg M., "Treatment of Deep Cartilage Defects in the Knee with Autologous Chondrocyte Transplantation", N. Eng. J. Med 1994; 331:889-895, Oct. 6, 1994; Freed C. R., "Transplantation of a Tissue-Engineered Pulmonary Artery", N. Eng. J. Med. 2001; 344:532-533. Shapiro A. M. J., Islet Transplantation in Seven Patients with Type 1 Diabetes Mellitus Using a Glucocorticoid-Free Immunosuppressive Regimen N. Eng. Med. 2000; 343:230-238. These references are hereby incorporated by reference.

Various delivery systems are known and can be used to administer the USSCs. Methods of introduction include but are not limited to intradermal, intramuscular, intraperitoneal, intravenous, subcutaneous, intranasal, epidural, and oral routes. The cells may be administered by any convenient route, for example by infusion or bolus injection, and may be administered together with other biologically active agents. Administration can be systemic or local.

In a specific embodiment, it may be desirable to administer the USSCs locally to the area in need of treatment for ischemic damage, or the risk thereof; this may be achieved by, for example, and not by way of limitation, local infusion during surgery, by injection, by means of a catheter, or by means of an implant, said implant being of a porous, nonporous, or gelatinous material, including membranes, such as sialastic membranes, or fibers. In another embodiment, the USSCs can be delivered in a vesicle, in particular a liposome (e.g., an encapsulated liposome).

Systemic Infusions

In instances where the number of USSCs in a single stored sample is insufficient, several such samples can be combined to provide the required number of cells. Alternatively, if the number of USSCs in a stored sample is more than sufficient, the sample can be aliquoted and one or more aliquots administered to the patient. The USSCs can be administered by infusion into the patient by, e.g., intracoronary infusion, retrograde venous infusion (see, e.g., Perin and Silva, *Curr. Opin. Hematol.* 11:399-403, 2004), intraventricular infusion, intracerebroventricular infusion, cerebrospinal infusion, and intracranial infusion.

It is anticipated that human therapy is likely to require one or more infusions of USSCs. Several infusions of USSCs can be administered over time, e.g., one on day one, a second on day five, and a third on day ten. After the initial ten day period, there can be a period of time, e.g., two weeks to 6 months without cell administration, after which time the ten-day administration protocol can be repeated.

Whether administered as a single infusion therapy or multiple infusion therapies, it is possible that the recipient will require immunosuppression. The protocols followed for this will follow the precedents now used in human transplantation for bone marrow replacement (i.e., cell transplantation), with such agents as cyclosporin A and FK506. Surprisingly, though, we have observed that the administration of USSCs does not usually require such immunosuppression.

Direct Injection

Another possible administration route for USSCs is via direct surgical injection (e.g., intramyocardial or transendocardial injection, intracranial, intracerebral, or intracisternal injection, intramuscular injection, intrahepatic injection, and intrapancreatic injection) into the tissue or region of the body to be treated (e.g., the brain, muscle, heart, liver, pancreas, and vasculature). This method of administration may also require multiple injections with treatment interruption intervals lasting from 2 weeks to 6 months, or as otherwise determined by the attending physician.

Implantation

USSCs can also be administered by implantation into a patient at the site of ischemic disease or injury or at a site that will facilitate treatment of the ischemic disease or injury.

Detailed Characterization of USSCs

USSCs are adherent cells with a fibroblastoid cell shape and two or three nucleoli obtained after trypsin EDTA-treatment and reseeding under appropriate culture conditions. The cells rapidly expand to confluence in a long, stretched morphology. The cells plated at low density demonstrate the fibroblastoid morphology of USSCs. These cells can readily be grown over greater than 14 culture passages. An almost confluent cell USSC layer shows a parallel orientation of cells. Morphologically, USSCs are approximately 30% larger than MSCs.

The surface marker phenotype of the primary adherent cell layer as well as all derivatives thereof in subsequent passages are and remain negative for the CD45 marker. CD45, a characteristic marker antigen for hematopoietic cell is almost not detectable in USSCs from later passages.

After in vitro culture, USSC preparations become positive for the stage-specific early antigen 4 (SSEA4) and show the homogenous expression of this embryonic marker. In a FACS analysis for SSEA4 embryonic marker, cells strongly show expression of the stage-specific early antigen 4 (SSEA4). At the same time, USSC cultures are negative for HLA-class I surface antigen expression, HLA-DR antigen expression, and CD14 expression. In a FACS analysis for HLA-class I, HLA DR, and CD14, USSCs are negative for HLA-class I antigens.

These cells are also negative for the HLA-DR and CD14 surface antigens, characteristic for antigen presenting cells (HLA-DR) and monocytes (CD14). USSCs are also negative for the CD106 surface antigen.

USSCs were grown in H5100/PEI for over 10 passages. During this culture period a significant increase of CD34 antigen expression was observed. In passage 3 until day 54, no CD34 positive cells can be detected. In contrast, in the seventh passage on day 82 a novel CD34 positive subpopulation appears. In contrast, when such CD34 or/and F1K1 positive progenitors were cultured with cytokine conditioned medium specific for hematopoietic differentiation, the typical mixed or hematopoietic colonies for red and white blood cell precursors (CFU-GM and BFU-E) developed comparable to $CD45^+$ hematopoeitic progenitor cells.

If cord blood mononuclear cells depleted for CD14 are cultured in high glucose containing medium, they exhibit the typical characteristics of neural stem cells. USSCs cultured in Dulbecco's modified eagle medium (DMEM) high glucose demonstrate an astrocyte-like morphology. After being expanded with PEI, USSCs express the neural stem cell marker nestin. A first observation indicates that nestin staining is less pronounced after cells have been stimulated with neural inducing agents like retinoid acid (RA), basic fibroblast growth factor bFGF, and nerve growth factor β (NGF-β) (McKay, 1997).

When USSCs are taken from any of the expansion passages and induced in DAG (dexamethasone, ascorbic acid, B-glycerol phosphate) containing culture conditions or in fibronectin containing medium, differentiation along the osteogenic lineage is induced. As shown in Table 2, bone specific marker genes (alkaline phosphatase, osteocalcin, collagen type I) are readily induced and detectable by RT-PCR.

TABLE 2

RT-PCR analysis during osteogenic differentiation of USSCs.

| | control | day 7 | day 14 |
|---|---|---|---|
| β-actin (pos. control) | + | + | + |
| alkaline phosphatase | − | + | + |
| collagen type II | − | + | + |
| osteocalcin | + | + | − |

All three marker genes of osteogenic differentiation show an increased mRNA expression at day 7 of DAG induction. B-actin serves as a positive control.

Mineralized nodule formation was observed after osteogenic induction and after staining with alizarin red. Osteogenic differentiation of nearly confluent USSC layers was induced by addition of dexamethasone, asorbic acid and B-glycerolphosphate to the culture medium H5100. At day 10 of stimulation characteristic bone nodules appear. Mineral deposition of these nodules can be demonstrated by Alizarin Red staining. Under these osteogenic induction conditions, the cells undergo complete osteogenic differentiation as demonstrated by accumulation of mineralized bone in distinct nodules, which can be stained with Alizarin Red. Alternatively, the accumulation of hydroxyapatite in the cell culture can be detected after six days by von Kossa staining.

Collection of Cord Blood (CB)

Collection of cord blood in a hospital obstetric department was performed with informed consent of the mother. After delivery of the baby with the placenta still in utero, the umbilical cord was doubly clamped and transected 7-10 cm away from the umbilicus. After disinfection of the cord, the umbilical vein was punctured and CB collected into collection bags containing citrate phosphate dextrose (CPD) as the antiocoagulant.

Isolation of Mononuclear Cells from Cord Blood

Umbilical cord blood was carefully loaded onto Ficoll a solution (density 1.077 g/cm$^3$), and a density gradient centrifugation was performed (450 g, room temperature, 25 min.). The mononuclear cells (MNC) of the interphase were collected and washed twice in phosphate buffer saline, pH7.3 (PBS).

Generation of Adherent Layers of Fibroblastoid Morphology

Mononuclear cells were plated out at a density of about 5×10$^3$ cells/cm$^2$ in T25 culture flasks (Nunclon) [A.) B.) C.)]. Four different culture methods were used to initiate growth of adherent stem cells:

A.) CD-derived MNCs were initially cultured in Myelocult H5100 medium (StemCell Technologies, Vancouver, Canada) containing 10$^{-7}$ M dexamethasone.

B.) CB-derived MNCs were initially cultured in Mesencult (StemCell Technologies, Vancouver, Canada) containing 10$^{-7}$ M dexamethasone.

C.) CB-derived MNCs were plated at a density of 5×10$^6$/ml in 10 ml Myelocult H5100 Medium (StemCell Technologies, Vancouver, Canada) into 50 ml culture-flasks (Nunclon) without dexamethasone.

All cultures were incubated at 37° C. in 5% $CO_2$ in a fully humidified atmosphere, and were fed once a week by removing the complete medium with the non-adherent cells and adding 10 ml of fresh medium. After several time points the adherent spindle-shaped cells were removed by treatment with 0.05% trypsin and 0.53 mM EDTA for 2 min, rinsed with 50% serum-containing medium, collected by centrifugation at 780 g and analyzed by flow cytometry or RT-PCR. After two to three weeks, adherent cells of fibroblastoid morphology appear in about 30% of all cell cultures.

Culture Conditions for the Expansion of USSCs

USSCs can be expanded in H5100 medium containing 10 ng/ml IFG I (Insulin-like growth factor-I), 10 ng/ml PDGF-BB (Platelet-derived growth factor-BB) and 10 ng/ml rh-human EGF (Recombinant Human epidermal growth factor) (PEI medium) at a density ranging from 1×10$^4$ and 1×10$^5$ cells/ml. Alternatively, USSC preparations can be expanded in the initial growth medium.

Immunophenotyping of Cells by Cytofluorometry

In order to determine the immunophenotype of USSCs, cells were stained with FITC-conjugated anti-CD45 (Becton Dickinson, Coulter), PE conjugated anti-CD14 (PharMingen, Coulter), anti-SSEA-4 (MC-813-70) labeled with goat F(ab')$_2$ anti-Mouse IgG+IgM (H+L)-FITC (Coulter), anti-CD10-PE (CALLA, PharMingen), anti-HLA-class I (, Coulter) labeled with goat F(ab')$_2$ anti-Mouse IgG+IgM (H+L)-FITC, andti-CD13-PE (Becton Dickinson, Coulter); anti-CD29 (Coulter), anti CD44 (Coulter), anti-CD49e (Coulter), anti-CD90 (Coulter), anti-HLA-class II-FITC (Coulter). Cells were analyzed using an EPICS XL (Coulter) or a FACS analyzer (Becton Dickinson).

In order to assess the angiogenic potential of USSCs, the present study evaluated the effect of USSCs on the reconstitution of blood flow in a murine ischemic hind limb model. Method: The proximal portion of the femoral artery of athymic NMRI nude mice (18-22 g, n=11) were electrically coagulated. After 24 hours, 2.5×10$^6$ USSC and buffer as control were intravenously injected. After two weeks, the ratio of blood flow in the ischemic and non-ischemic limb was determined by using a laser Doppler blood flow imager (LDI) for each individual animal. A swimming test was used to access alterations in the exercise capacity of USSC-treated ischemic limbs. Engraftment of USSCs, number and size of conductant vessels, and reduction of atrophic muscle tissue were examined histologically.

Results: Two weeks after induction of limb ischemia, LDI revealed a significantly enhanced recovery of limb perfusion in mice treated with USSC (0.60±0.21; P<0.001 versus 0.31±0.14). Consistently, the USSC group showed a significantly greater exercise capacity with a swimming time ratio (swimming time prior and 14 days after induction of ischemia) of 0.89±0.15; P=0.001 versus control (0.48±0.17; n=11). In situ hybridization analysis revealed engraftment of USSC within the ischemic hind limb, mostly adjacent to vascular wall. The number of vessels was significantly increased in USSC group as compared to the control for small (<50 um: 3.7±0.7 versus 4.7±0.3) and larger vessels (>100 um: 0.3±0.3 versus 0.9±0.3) whereas for middle sized vessels (50-100 um; 3.0±1.0 versus 2.9±0.6) no difference was observed. Finally, the proportion of atrophic muscle tissue was significantly lower in USSC treated animals than in the control group (8.1±2.5% versus 22.7±1.7%; P=0.0001).

These data demonstrate that treatment of tissue ischemia with USSCs in a murine model of hind limb ischemia significantly enhances recovery of limb perfusion and consequently enhances the exercise capacity by maintaining healthy muscle tissue. Therefore, this study suggests that USSCs are a promising candidate to enhance antiogenesis following acute ischemic tissue, e.g. after myocardial infarction.

What is claimed is:

1. A method for treating or reducing the risk of ischemia in a tissue of a human with compromised blood flow to said tissue comprising administering one or more human unrestricted somatic stem cells (USSCs) to said human by a method selected from the group consisting of local administration to said tissue and systemic infusion, wherein said USSCs are negative for CD14 and CD45 antigen expression, positive for CD13 and CD29 antigen expression, and lack expression of hyaluronan synthase.

2. The method of claim 1, wherein said USSCs are administered to said human systemically.

3. The method of claim 2, wherein said USSCs are administered intravenously.

4. The method of claim 1, wherein said tissue is limb tissue which has been rendered ischemic by compromised blood flow to said limb tissue.

5. The method of claim 1, wherein said tissue is tissue of an internal organ.

6. The method of claim 1, wherein said ischemia is treated or the risk of said ischemia is reduced by engraftment of said USSCs in said tissue such that the number of blood vessels supplying blood to said tissue is increased.

7. The method of claim 6, wherein the increase in blood vessel number results in a decrease in necrosis in said tissue.

8. The method of claim 7, wherein said tissue is muscle, and the increase in blood vessel number decreases the amount of atrophic muscle.

9. The method of claim 8, wherein said muscle is skeletal muscle.

10. The method of claim 9, wherein said muscle is limb muscle.

11. The method of claim 8, wherein said muscle is cardiac muscle.

12. The method of claim 8, wherein said muscle is smooth muscle.

13. The method of claim 1, wherein said USSCs are derived from umbilical cord blood.

14. The method of claim 1, wherein said USSCs are administered locally.

15. The method of claim 14, wherein said USSCs are administered intramuscularly.

16. The method of claim 1, wherein said USSCs are administered directly into said tissue.

17. The method of claim 16, wherein said tissue is selected from the group consisting of brain, muscle, heart, liver, pancreas, and vasculature.

\* \* \* \* \*

UNITED STATES PATENT AND TRADEMARK OFFICE
CERTIFICATE OF CORRECTION

PATENT NO. : 8,613,906 B2  Page 1 of 1
APPLICATION NO. : 11/915660
DATED : December 24, 2013
INVENTOR(S) : Muhs et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1620 days.

Signed and Sealed this
Twenty-second Day of September, 2015

Michelle K. Lee
*Director of the United States Patent and Trademark Office*